(12) United States Patent
Weksler et al.

(10) Patent No.: US 6,815,175 B2
(45) Date of Patent: Nov. 9, 2004

(54) ANTI-AMYLOID PEPTIDE ANTIBODY BASED DIAGNOSIS AND TREATMENT OF A NEUROLOGICAL DISEASE OR DISORDER

(75) Inventors: Marc E. Weksler, Paris (FR); Paul Szabo, Linden, NJ (US)

(73) Assignee: Cornell Research Foundation, Inc., Ithaca, NY (US)

( * ) Notice: Subject to any disclaimer, the term of this patent is extended or adjusted under 35 U.S.C. 154(b) by 15 days.

(21) Appl. No.: 10/099,880

(22) Filed: Mar. 14, 2002

(65) Prior Publication Data

US 2004/0197831 A1 Oct. 7, 2004

Related U.S. Application Data

(60) Provisional application No. 60/276,659, filed on Mar. 16, 2001.

(51) Int. Cl.[7] .................. G01N 33/53; G01N 33/567; G01N 33/542; C07K 16/00; A61K 38/00
(52) U.S. Cl. .................. 435/7.92; 435/7.9; 435/7.21; 435/7.1; 530/300; 530/387.1
(58) Field of Search ................. 435/7.92, 7.9, 435/7.21, 7.1; 530/300, 387.1

(56) References Cited

U.S. PATENT DOCUMENTS

| | | | |
|---|---|---|---|
| 4,946,778 A | 8/1990 | Ladner et al. | 435/69.6 |
| 5,132,405 A | 7/1992 | Huston et al. | 530/387.3 |
| 5,270,165 A | 12/1993 | Van Nostrand et al. | 435/7.1 |
| 5,427,931 A | 6/1995 | Van Nostrand et al. | 435/70.2 |
| 5,476,786 A | 12/1995 | Huston | 435/252.33 |
| 5,679,531 A | 10/1997 | König et al. | 435/7.1 |
| 5,693,478 A | 12/1997 | Vitek et al. | 435/7.1 |
| 5,693,753 A | 12/1997 | König et al. | 530/344 |
| 5,786,180 A | 7/1998 | König et al. | 435/70.21 |
| 6,194,163 B1 | 2/2001 | Doyle et al. | 435/7.92 |
| 6,218,506 B1 | 4/2001 | Krafft et al. | 530/324 |
| 6,221,645 B1 | 4/2001 | Chrysler et al. | 435/226 |

FOREIGN PATENT DOCUMENTS

| | | | |
|---|---|---|---|
| EP | 085159 | 10/1988 | C12P/21/00 |
| EP | 0391714 | 10/1990 | G01N/33/68 |
| EP | 683234 A1 | 11/1995 | C12P/21/08 |
| EP | 0783104 A1 | 7/1997 | G01N/33/68 |
| EP | 0872558 A1 | 10/1998 | C12P/21/08 |
| FR | 2 770 217 | 4/1999 | C07K/14/47 |
| WO | WO89/12690 A1 | 12/1989 | |
| WO | WO90/12870 A1 | 11/1990 | |
| WO | WO90/12871 A1 | 11/1990 | |
| WO | WO96/25435 A1 | 8/1996 | |
| WO | WO96/34099 A2 | 10/1996 | |
| WO | WO97/27296 A1 | 7/1997 | |
| WO | WO98/03643 A2 | 1/1998 | |
| WO | WO98/44955 A1 | 10/1998 | |
| WO | WO98/58060 A1 | 12/1998 | |
| WO | WO99/27944 A1 | 6/1999 | |
| WO | WO00/77178 A1 | 12/2000 | |
| WO | WO01/12598 A2 | 2/2001 | |
| WO | WO01/35106 A2 | 5/2001 | |
| WO | WO01/90182 A2 | 11/2001 | |

OTHER PUBLICATIONS

Hardy et al., 1998, Science, vol. 282, pp. 1075–1079.*
Motter et al. 1995, Annals of Neurology, vol. 38, No. 4, pp. 643–648.*
Clark et al., 1993, Arch. Neurology, vol. 50, pp. 1164–1172.*
DeMattos et al., Science, 2002, 295:2264–2267.
Bacskai et al., Nature Medicine, 2001, 7:369–372.
DeMattos et al., PNAS, 2001, 98(15):8850–55.
Du et al., Neurology, 2001, 57:801–805.
Hyman et al., 2001, Ann Neurol, 49:808–810.
Monsonego et al., Proc. Natl. Acad. Sci. USA, 2001, 98:10273–10278.
Selkoe, Neuron, 2001, 32:177–180.
Town et al., Neuroscience Letters, 2001, 307: 101–104.
Bard et al., Nature Medicine, 2000, 6(8):916–19.
Chen et al., Nature, 2000, 408:975–79.
Grubeck–Loebenstein et al., TINS, 2000, 23:114.
Gouras et al., Am J Pathol, 2000, 156:15–20.
Janus et al., Nature, 2000, 408:979–982.
Morgan et al., Nature, 2000, 408:982–985.
Selkoe, Nature Bio., 2000, 18:823–24.
Weiner et al., Annals of Neurology, 2000, 48:567–79.
Bohrmann et al., The Journal of Biological Chem, 1999, 274:15990–15995.
Schenk et al., Nature, 1999, 400:173–77.
Carlson et al., Human Molec Genetics, 1997, 6:1951–1959.
Singh, Gerontology, 1997, 43:79–94.
Trieb et al., Neurobiol. Aging, 1996, 17(4):541–47.
Games et al., Nature, 1995, 373:523–527.
Amiel, The Lancet, 1993, 341:1249–50.
Rozemuller et al., Am. J. Pathol., 1993, 142(5):1449–57.
Corder et al., Science, 1993, 261:921–923.
Fraser et al., Biochem. 1992, 31:10716–23.
Haan et al., Clin. Neuro. Neurosurg., 1992, 94:317–8.
Roos et al., Ann. N.Y. Acad. Sci., 1991, 640:155–60.
Haan et al., Clin. Neurol. Neurosurg., 1990, 92:305–10.
Haan et al., Arch. Neurol., 1990, 47:965–7.
Levy et al., Science, 1990, 248:1124–26.
Timmers et al., Neurosci. Lett., 1990, 118:223–6.
Frangione, Ann. Med., 1989, 21:69–72.
Glenner et al., Journal of the Neurol. Sci., 1989, 94:1–28.
Huse et al., Science, 1989, 246:1275–81.
Cooper et al., Proc. Natl. Acad. Sci. USA, 1988, 85:7763–66.
Coria et al., Lab. Invest., 1988, 58(4):454–8.
Cooper et al., Proc. Natl. Acad. Sci. USA, 1987, 84:8628–32.
Westermark et al., Proc. Natl. Acad. Sci. USA, 1987, 84:3881–85.
Westermark et al., Am. J. Pathology, 1987, 127(3):414–17.

* cited by examiner

Primary Examiner—Olga N. Chernyshev
(74) Attorney, Agent, or Firm—Darby & Darby

(57) ABSTRACT

The invention provides a method for assessing risk of a neurodegenerative disease or disorder in a subject. The method comprises comparing a level of anti-β-amyloid-42 (Aβ$_{42}$) antibody in a biological sample from a subject to a normal level, wherein a lower level in the biological sample from the subject indicates the risk of the disease or disorder. In a specific embodiment, the disease or disorder is Alzheimer's Disease (AD).

8 Claims, No Drawings

ANTI-AMYLOID PEPTIDE ANTIBODY BASED DIAGNOSIS AND TREATMENT OF A NEUROLOGICAL DISEASE OR DISORDER

This application claims priority under 35 U.S.C. § 1.119 (e) to provisional application Ser. No. 60/276,659, filed Mar. 16, 2001, which is incorporated herein by reference in its entirety.

This research leading to the present invention was supported, in part, by National Institutes of Health Grant No. AG 14669. Accordingly, the U.S. Government has certain rights in this invention

BACKGROUND OF THE INVENTION

The deposition of amyloid beta 42 amino acid peptide ($A\beta_{42}$), a toxic cleavage product of the transmembrane amyloid precursor protein (APP), in the brain of patients with Alzheimer's disease (AD) is thought to play a pathogenic role in the disease. Much evidence is consistent with this hypothesis: (i) the appearance of large numbers of amyloid plaques in the brains of patients with AD, (ii) early onset of AD in persons with trisomy 21, (iii) the early onset of AD in humans with a mutated APP gene, and (iv) the appearance of amyloid plaques in the brain and cognitive impairment in mice expressing a mutant, human APP-transgene. However, at present physicians have no way to directly detect amyloid plaques, leaving an AD diagnosis solely to a neurological examination. Except for family history or APOE4 status, physicians cannot predict who is likely to develop AD. Moreover, until very recently, therapeutic approaches to AD were limited to maintaining cholinergic function, using anti-cholinesterase inhibitors such as Aricept, or to attempt to decrease the generation of AB42 from APP.

Recently, a new paradigm for the therapy of AD was suggested by the finding that immunization of APP transgenic mice with $A\beta_{42}$ decreased cerebral amyloid deposits. This suggested that immune clearance of $A\beta_{42}$ from the brain might also be a rational therapeutic approaches to AD. Subsequently Bard's group reported that the administration of murine anti-amyloid-beta peptide ($A\beta_{42}$) antibodies to the APP transgenic moused model of Alzheimer's Disease (AD) decreases cerebral amyloid deposition.

While interesting, these results raised the question: if murine anti-A$\beta$42 antibodies can prevent amyloid deposition in the brains of APP transgenic mice, what is the relationship to humans? The clinical trial results of treating AD by immunization with A$\beta$ peptide dashed hopes for this approach in humans. Volunteers developed r brain inflammation having characteristics of encephalitis or meningitis, prompting by suspension of the trial (Weiss, The Washington Post, Sunday Mar. 2, 2002, p. A3).

Accordingly, a significant need remains to diagnose and treat AD in humans. The present invention addresses this need through the discovery of naturally occurring anti-A$\beta$ antibodies that appear to be protective.

SUMMARY OF THE INVENTION

There is a need in the art for identifying whether someone is at risk for, or has, a neurological disease or disorder. For example, the only definitive diagnosis for Alzheimer's Disease occurs upon visual inspection of the brain during autopsy; other than family history or ApoE4 status, there is no way to assess our individuals of developing AD risk. The invention provides a great advance: a method for assessing risk of, including diagnosing, neurological diseases or disorders such as AD, and for effectively clearing amyloid plaques.

The present invention advantageously provides method for assessing risk of a immune deficiency or disorder in a subject, which leads to a neurodegenerative disease or disorder. This method comprises comparing a level of anti-amyloid peptide antibody in a biological sample from a subject to a normal level, wherein a lower level in the biological sample from the subject indicates the presence of the disease or disorder. In a specific embodiment, the disease or disorder is Alzheimer's Disease (AD); in a further specific embodiment, the amyloid peptide is $\beta$-amyloid-42 ($A\beta_{42}$).

The biological sample can be blood, serum, or plasma.

The normal level can be determined from an average of the level of anti-amyloid peptide antibody in the biological sample from a population of age-matched normal subjects who do not show any symptoms of the immune deficiency or disorder, or from an average of the level of anti-amyloid peptide antibody in the biological sample from a population of all subjects, including subjects who do not show any symptoms of the immune deficiency or disorder, or from a single normal to sample.

In a preferred aspect, the method comprises determining the level of anti-amyloid peptide antibody in the biological sample by immunoassay, e.g., enzyme-linked immunosorbent assay.

In addition, the discovery of naturally occurring anti-A$\beta$ antibodies, which presumably cross the blood brain barrier with some facility in order to bind to and affect A$\beta$, provides a source of imaging agents, e.g., for position emission tomography (PET) scanning.

The surprising observation that certain neurological diseases or disorders are associated with a deficiency of anti-amyloid antibodies leads to an advantageous method of treating such an immune deficiency or disorder in a subject, which leads to a neurodegenerative disease or disorder. This method comprises administering a therapeutically effective amount of a human anti-amyloid peptide antibody to a subject believed to suffer from the immune deficiency or disorder. For example, the disease or disorder can be Alzheimer's Disease (AD). In such an embodiment, the amyloid peptide can be $\beta$-amyloid-42 ($A\beta_{42}$).

In a specific embodiment, the antibody is a monoclonal antibody, e.g., a humanized antibody, or an antibody from and EBV transformed cell, preferably obtained from a normal patient. In another embodiment, the antibody is a polyclonal antibody purified from normal or healthy serum. It is also possible to generate such an antibody from combinatorial 1 g phage display libraries, and from xeno mice.

A therapeutically effective amount of the antibody can be an amount that provides a level of the antibody in a biological sample from the subject that is at least the same as or greater than a normal level. The level of therapeutic anti-amyloid peptide antibody in a biological sample can be determined by immunoassay, e.g., enzyme-linked immunosorbent assay. Examples of a biological sample include blood, go serum, or plasma, or cerebral spinal fluid (CSF). In specific embodiments, the normal level is determined from an average of the level of anti-amyloid peptide antibody in the biological sample from a population of age-matched normal subjects or a population of all subjects who do not show any symptoms of the immune deficiency or disorder.

DETAILED DESCRIPTION

This invention pertains to the unexpected discovery that normal humans have anti-amyloid antibodies, and that humans with low levels of serum anti-$A\beta_{42}$ antibodies might be at that increased risk of AD. The results described in the Examples demonstrate this. Thus, AD and other neurological diseases or disorders may be an immune deficiency disease which can be predicted or diagnosed by detecting low serum levels of anti-amyloid antibody, and treated by restoring the anti-amyloid antibody deficit, e.g., to normal levels or above. Preferably, the "replacement" antibodies are effective in humans, e.g., "human antibodies".

A neurological (i.e., neurodegenerative) disease or disorder is associated with amyloidosis when amyloid deposits or amyloid plaques are found in or in proximity to tissues affected by the disease, or when the disease is characterized by overproduction of a protein, particularly an amyloid protein, that is or can become insoluble. The amyloid plaques may provoke pathological effects directly or indirectly by known or unknown mechanisms. Examples of amyloid diseases include, but are not limited to, systemic diseases, such as chronic inflammatory illnesses, multiple myeloma, macroglobulinernia, familial amyloid polyneuropathy (Portuguese) and cardiomyopathy (Danish), systemic senile amyloidosis, familial amyloid polynephropathy (Iowa), familial amyloidosis (Finnish), Gerstmann-Straussler-Scheinker syndrome, familial amyloid nephropathy with urticaria and deafness (Muckle-Wells syndrome), medullary carcinoma of thyroid, isolated atrial amyloid, and hemodialysis-associated amyloidosis (HAA); and amyloid associated neurodegenerative diseases.

As noted above, in addition to systemic amyloidosis, the present invention relates particularly to neurodegenerative diseases involving amyloidosis. The term "neurodegenerative disease" (or "neurological disease") refers to a disease or disorder of the nervous system, particularly involving the brain, that manifests with symptoms characteristic of brain or nerve dysfunction, e.g., short-term or long-term memory lapse or defects, dementia, cognition defects, balance and coordination problems, and emotional and behavioral deficiencies. Such diseases are "associated with amyloidosis" when histopathological (biopsy) samples of brain tissue from subjects who demonstrate such symptoms would reveal amyloid plaque formation. As biopsy samples from brain, especially human brain, are obtained with great difficulty from living subjects or might not be available at all, often the association of a symptom or symptoms of neurodegenerative disease with amyloidosis is based on criteria other than the presence of amyloid deposits, such as plaques or fibrils, in a biopsy sample. Thus, particularly with respect to AD, traditional diagnosis depends on symptomology and, if relevant, family history. In clinical practice a physician will diagnose Alzheimer's Disease on the basis of symptoms of senile dementia, including cognitive dysfunction, retrograde amnesia (loss of memory for recent events), progressive impairment of remote memory, and possibly depression or other neurotic syndromes. The individual presents with slow disintegration of personality and intellect. Imaging may reveal large cell loss from the cerebral cortex and other brain areas. AD differs from senile dementia, however, by age of onset: AD is likely to occur in the fifth or sixth decade, whereas senile dementia occurs in the eighth decade or later.

This invention provides a method for diagnosing AD patients or identifying those at risk of developing AD. In particular, low serum levels of anti-amyloid, e.g., $A\beta_{42}$, antibodies indicates a predisposition to developing or the presence of a neurodegenerative disease or disorder. The key advantage over current clinical at diagnostic practice is early detection: detecting low levels of anti-Aβ antibodies can predict the onset of AD before the appearance of symptoms such as cognitive and memory dysfunction. Thus, low serum anti-Aβ antibody levels are a risk factor for AD.

Furthermore, because the anti-AD antibodies presumably bind amyloid in the brain, they must be able to cross the blood brain barrier and recognize the Aβ with a high degree of specificity (to avoid undesirable cross-reaction with healthy brain tissues, which could cause inflammation). Such targeting specifity renders the natural antibodies of the invention particularly useful for diagnostic imaging of amyloid plaques in human brain. By labeling the antibodies with an appropriate radioisotope, it is possible to use imaging techniques like PET for a definitive diagnosis of a neurodegenerative disease, such as AD.

In a specific embodiment, according to the present invention the neurodegenerative disease associated with amyloidosis is Alzheimer's disease (AD), a condition that includes sporadic AD, ApoE4-related AD, other mutant APP forms of AD (e.g., mutations at APP717, which are the most common APP mutations), mutant PS1 forms of familial AD (FAD) (see, WO 96/34099), mutant PS2 forms of FAD (see, WO 97/27296), and alpha-2-macroglobulin-polymorphism-related AD. In other embodiments, the disease may be the rare Swedish disease characterized by a double KM to NL mutation in amyloid precursor protein (APP) near the amino-terminus of the βAP portion of APP (Levy et al., 1990, Science 248:1124–26). Another such disease is hereditary cerebral hemorrhage with amyloidosis (HCHA or HCHWA)-Dutch type (Rozemuller et al., 1993, Am. J. Pathol. 142:1449–57; Roos et al., 1991, Ann. N.Y. Acad. Sci. 640:155–60; Timmers et al., 1990, Neurosci. Lett. 118:223–6; Haan et al., 1990, Arch. Neurol. 47:965–7). Other such diseases known in the art and within the scope of the present invention include, but are not limited to, sporadic cerebral amyloid angiopathy, hereditary cerebral amyloid angiopathy, Downs syndrome, Parkinson-dementia of Guam, and age-related asymptomatic amyloid angiopathy (see, e.g., Haan and Roos, 1990, Clin. Neurol. Neurosurg. 92:305–310; Glenner and Murphy, 1989, N. Neurol. Sci. 94:1–28; Frangione, 1989, Ann. Med. 21:69–72; Haan et al., 1992, Clin. Neuro. Neurosurg. 94:317–8; Fraser et al., 1992, Biochem. 31:10716–23; Coria et al., 1988, Lab. Invest. 58:454–8). The actual amino acid composition and size of the RAP involved in each of these diseases may vary, as is known in the art (see § above, and Wisniewski et al., 1991, Biochem. Biophys. Res. Commun. 179:1247–54 and 1991, Biochem. Biophys. Res. Commun. 180:1528 [published erratum]; Prelli et al., 1990, Biochem. Biophys. Res. Commun. 170:301–307; Levy et al., 1990, Science 248:1124–26).

Amyloid

The terms "amyloid," "amyloid plaque," and "amyloid fibril" refer generally to insoluble proteinaceous substances with particular physical characteristics independent of the composition of proteins or other molecules that are found in the substance. Amyloid can be identified by its amorphous structure, eosinophilic staining, changes in thioflavin fluorescence, and homogeneous appearance. Protein or peptide components of amyloid are termed herein "amyloid polypeptides," and include, but are not limited to, β-amyloid peptide (Aβ), including synthetic βAPs corresponding to the first 28, 40, or 42 amino acids of Aβ, i.e., Aβ(1–28) or Aβ028, Aβ(1–40) or Aβ40, Aβ(1–42) or Aβ42, respectively, as well as a synthetic βAP corresponding to amino acids 25–35 of Aβ, i.e., $A\beta_{25-35}$. Other amyloid peptides include scrapie protein precursor or prion protein (associated with Creuzfeldt-Jacob's disease); synuclein (associated with Parkinson's disease), Huntington's protein (associated with Huntington's chorea), immunoglobulin, including K or A light or heavy chains, or fragments thereof, produced by myelomas; serum amyloid A; β2-microglobulin; ApoA1; gelsolin; cystatin C; (pro)calcitonin; atrial natururetic factor; islet amyloid polypeptide, also known as amylin (see, Westermark et al., Proc. Natl. Acad. Sci. USA 84:3881–85, 1987; Westermark et al., Am. J. Physiol. 127:414–417, 1987; Cooper et al., Proc. Natl. Acad. Sci. USA 84:8628–32, 1987; Cooper et al., Proc. Natl. Acad. Sci. USA 85:7763–66, 1988; Amiel, Lancet 341:1249–50, 1993); and the like. In a specific aspect, the term "amyloid" is used herein to refer to substances that contain Aβ. "Amyloidosis" refers to the in vivo deposition or aggregation of proteins to form amyloid plaques or fibrils.

The 42 amino acid (4.2 kDa) beta-Amyloid Peptide $A\beta_{42}$ or βAP) derives from a family of larger Amyloid Peptide Precursor (APP) proteins (Glenner and Wong, 1984, Biochem. Biophys. Res. Commun. 120:885–890; Glenner and Wong, 1984, Biochem. Biophys. Res. Commun. 122:1131–35; Goldgaber et al., 1987, Science 235:8778–8780; Kang et al., 1987, Nature 325:733–736; Robakis et al., 1987, Proc. Natl. Acad. Sci. USA 84:4190–4194; Tanzi et al., 1987, Science 235:880–884). APP is a transmembrane protein found in a number of isoforms, which in general are referred to herein as full length APP (flAPP). In addition, there is a soluble form of APP (sAPPα), formed by the action of β-secretase (discussed supra).

The "level of Aβ" in a biological sample can be detected by any method known in the art, including by not limited to immunoassay (as exemplified infra), biochemical analysis (e.g., purification, gel electrophoresis, quantitative amino acid sequence analysis or composition analysis, Congo red or Thioflavin-T staining, and the like), or other methods known to detect Aβ. In particular, fluorescence methods using Thioflavin T are used to detect aggregated peptide. A "biological sample" includes, but is not limited to body fluids (blood, blood cells, plasma, serum, cerebrospinal fluid, urine), tissues (e.g., spinal chord, nerves, etc.), or organs (preferably brain, but also including liver, kidney, pancreas, etc.).

Antibodies to Amyloid Peptides

According to the invention, anti-amyloid peptide, i.e., produced recombinantly or by chemical synthesis, and fragments or other derivatives or analogs thereof, including fusion proteins, may be used as an antigen to detect and to purify, and in some instances as an immunogen to generate, natural antibodies that recognize the amyloid peptide. As used herein, the term "natural antibody" (whether singular or plural) refers to an antibody having the functional characteristics of serum antibodies found in normal human subjects. Such antibodies can include but are not limited to polyclonal, monoclonal, chimeric, single chain, Fab fragments, and an Fab expression library. The anti-amyloid peptide antibodies of the invention may be cross reactive, e.g., they may recognize amyloid peptide from different species. Polyclonal antibodies have greater likelihood of cross reactivity. Alternatively, an antibody of the invention may be specific for a single form of amyloid peptide, such as an anti-human βamyloid-42 peptide. Such an antibody is effective in human, e.g., a human (including humanized and chimeric) antibody.

Various procedures known in the art may be used for the production of polyclonal antibodies to amyloid peptide. Sera from a normal individual or pooled sera from a group of normal individuals, provides a source of amyloid protective anti-amyloid antibody. Purification of antibodies can be achieved by standard techniques for immunoglobulin production, as is well known in the art.

For preparation of monoclonal antibodies directed toward the amyloid peptide, any technique that provides for the production of antibody molecules by continuous human or human hybridoma cell lines in culture may be used. These include, but are not limited to, the hybridoma technique originally developed by Kohler and Milstein (Nature 256:495–497, 1975), as well as the trioma technique, the human B-cell hybridoma technique (Kozbor et al., Immunology Today 4:72, 1983; Cote et al., Proc. Natl. Acad. Sci. U.S.A. 80:2026–2030, 1983), and the EBV-hybridoma technique to produce human monoclonal antibodies (Cole et al., in Monoclonal Antibodies and Cancer Therapy, Alan R. Liss, Inc., pp. 77–96, 1985). In an additional embodiment of the invention, monoclonal antibodies can be produced in germ-free animals (PCT Publication No. WO 89/12690). In fact, according to the invention, techniques developed for the production of "chimeric antibodies" (Morrison et al., J. Bacteriol. 159:870, 1984; Neuberger et al., Nature 312:604–608, 1984; Takeda et al., Nature 314:452–454, 1985) by splicing the genes from a mouse antibody molecule specific for an anti-amyloid peptide polypeptide together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

In a specific embodiment, anti-amyloid peptide antibody can be obtained from EBV transformed cells isolated from individuals who are protected from amyloidosis, i.e., have normal or elevated anti-amyloid antibody levels. Alternatively the antibodies can be isolated from normal serum using any of the multitude of techniques known in the art. These "natural" antibodies have the advantage of expected efficacy: they are protective in normal subjects, and their absence can lead to development of degenerative neuropathies characterized by amyloidosis.

According to the invention, techniques described for the production of single chain antibodies (U.S. Pat. Nos. 5,476,786 and 5,132,405 to Huston; U.S. Pat. No. 4,946,778) can be adapted to produce amyloid peptide specific single chain antibodies. Indeed, these genes can be delivered for expression in vivo. An additional embodiment of the invention utilizes the techniques described for the construction of Fab expression libraries (Huse et al., Science 246:1275–1281, 1989) to allow rapid and easy identification of monoclonal Fab fragments with the desired specificity for an amyloid peptide, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

Assays for the anti-β amyloid antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an amyloid peptide, one may assay generated hybridomas for a product which binds to an amyloid peptide fragment containing such epitope.

Pharmaceutical Compositions and Administration

As noted above, clinical testing of an $A\beta_{42}$-peptide vaccine resulted in brain inflammation in a number of patients. The present invention involves recognition that individuals with normal levels of anti-amyloid antibodies seem to be is protected from neurodegenerative disease without developing brain inflammation. Thus, delivery of natural anti-amyloid antibodies, i.e., passive immunization, to subjects at risk for or suffering from a neurodegenerative disease, e.g., AD, has greater potential for safety as well as efficacy.

The anti-amyloid peptide antibody of the invention can be formulated in a pharmaceutical composition with a pharmaceutically acceptable carrier. The phrase "pharmaceutically acceptable" refers to molecular entities and compositions a that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E.W. Martin.

A composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

According to the invention, the anti-amyloid antibody formulated in a pharmaceutical composition of the invention can be introduced parenterally, transmucosally, e.g., orally (per os), nasally, or rectally, or transdermally. Parental routes include intravenous, intra-arteriole, intramuscular, intradermal, subcutaneous, intraperitoneal, intraventricular, and intracranial administration. Preferably, administration is directly into the cerebrospinal fluid, e.g., by a spinal tap.

In another embodiment, the therapeutic compound can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss: New York, pp. 353–365 (1989); Lopez-Berestein, ibid., pp. 317–327; see generally ibid. To reduce its systemic side effects, this may be a preferred method for introducing the compound.

In yet another embodiment, the therapeutic compound can be delivered in a controlled release system. For example, a polypeptide may be administered using intravenous infusion with a continuous pump, in a polymer matrix such as poly-lactic/glutamic acid (PLGA), a pellet containing a mixture of cholesterol and the anti-amyloid peptide antibodycompound (SilasticR™; Dow Corning, Midland, Mich.; see U.S. Pat. No. 5,554,601) implanted subcutaneously, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)). Preferably, a controlled release device is introduced into a subject in proximity of the site of amyloidosis. Other controlled release systems are discussed in the review by Langer (Science 249:1527–1533 (1990)).

The therapeutic compositions and regimens of the invention are useful for treating a neurological disease or disorder associated with a deficiency of anti-amyloid antibodies. Thus, the "neurological diseases or disorder" of the invention is a neuropathy involving amyloid deposition, and associated with specific or general immunodeficiency. These diseases include, but are not limited to, Alzheimer's Disease; Kuru, Creuzdfelt-Jacob's disease, and other spongiform encephalopathies; Parkinson's Disease; and Huntington's chorea. The therapeutic regimens, specifically passive immunization with protective human antibodies against the amyloid peptide, are unexpectedly effective because they preferably employ anti-amyloid antibodies from normal individuals who seem to have protective immunity against amyloid deposition. These antibodies supplement the deficiency associated with the neurological disease or disorder.

Dosage and Regimen

A constant supply of the anti-amyloid peptide antibody can be ensured by providing a therapeutically effective dose (i.e., a dose effective to induce metabolic changes in a subject) at the necessary intervals, e.g., daily, every 12 hours, etc. These parameters will depend on the severity of the disease condition being treated, other actions, such as diet modification that are implemented, the weight, age, and sex of the subject, and other criteria, which can be readily determined according to standard good medical practice by those of skill in the art. Preferably, the anti-amyloid peptide antibody is administered for at least ten days, more preferably at least 100 days, and more preferably still, for the life of the recipient.

The term "prevent the onset of" means to prophylactically interfere with a pathological mechanism that results in the disease or disorder. In the context of the present invention, such a pathological mechanism can be an increase in processing of the amyloidogenic form of APP; dysregulation of $A\beta$ clearance; or some combination of the two. The term "ameliorate" means to cause an improvement in a condition associated with the disease or disorder. In the context of the present invention, amelioration includes a reduction in the level of $A\beta$, regulation of the formation of $A\beta$, decrease in aggregation of $A\beta$ or the formation of amyloid plaques, or improvement of a cognitive defect in a subject suffering from a disease or disorder associated with amyloidosis, e.g., Alzheimer's disease or an animal model of Alzheimer's disease. The phrase "therapeutically effective amount" or "dose" is used herein to mean an amount or dose sufficient to reduce the level of amyloid peptide, e.g., by about 10 percent, preferably by about 50 percent, and more preferably by about 90 percent. Preferably, a therapeutically effective amount can ameliorate or prevent a clinically significant deficit in the activity, function, and response of the host. Alternatively, a therapeutically effective amount is sufficient to cause an improvement in a clinically significant condition in the host.

A subject who "has an increased risk of developing" a neurological disease or disorder associated with amyloidosis may have a genetic predisposition to developing an amyloidosis, such as a person from a family that has members with familial Alzheimer's Disease (FAD). Alternatively, someone in his or her seventh or eighth decade is at greater risk for age-related AD.

A subject who "shows a symptom of" a neurological disease or be disorder associated with amyloidosis presents with a symptom or complaint found in subjects who have or have had such a disease or disorder. For example, in Alzheimer's Disease, these symptoms can include development of dementia, memory defects, and the like in the fifth and sixth decade, as discussed above.

An "$A\beta$ level reducing dose" is an amount of anti-amyloid peptide antibody that causes a decrease in the level of $A\beta$. Dosages can range from about 0.5 $\mu$g anti-amyloid peptide antibody per kg body weight to ($\mu$g/kg) to about 50 mg/kg, per day; preferably from about 5 $\mu$g/kg to about 10 mg/kg, per day. The amount of anti-amyloid peptide antibody used to decrease the level of $A\beta$ can be an amount corresponding to the level of anti-amyloid peptide antibody in a biological sample, especially blood (including plasma and serum) and CSF, from a normal subject.

A subject in whom administration of the anti-amyloid peptide antibody is an effective therapeutic regiment for a disease or disorder associated with amyloidosis is preferably a human.

"Reducing a level of amyloid-$\beta$ ($A\beta$) peptides" specifically refers to decreasing the amount of $A\beta 40$ or, preferably, $A\beta 42$, or more preferably, both, in vivo. $A\beta$ can accumulate in blood, cerebrospinal fluid, or organs. The primary organ of interest for reducing the level of $A\beta$ is brain, but $A\beta$ levels may also be reduced in body fluids, tissues, and/or other organs by the practice of this invention.

As used herein, the term "about" or "approximately" means within 50% of a given value, preferably within 20%, more preferably within 10%, more preferably still within 5%, and most preferably within 1% of a given value. Alternatively, the term "about" or "approximately" means that a value can fall within a scientifically acceptable error range for that type of value, which will depend on how quantitative a measurement can be given the available tools.

EXAMPLE 1

Low Anti-Amyloid Antibodies in Alzheimer's Disease

Late onset Alzheimer's disease (AD) is associated with increased deposits of $\beta$-amyloid peptide ($A\beta_{42}$ in the brain although serum $A\beta_{42}$ levels remain normal. Transgenic mice expressing a mutated, human amyloid precursor protein (APP) gene develop deposits of AP in their brain as they age and are a useful experimental model of human AD. When such transgenic mice are immunized with $A\beta_{42}$ in a modified Freund's adjuvant or passively immunized by giving murine anti-$A\beta_{42}$, deposition of $A\beta_{42}$ in the brain is significantly reduced (Schenk et al, Nature 1999, 400:173–7; Bard et al, Nat. Med. 2000, 6:916–9). Recently, immune-mediated reduction of cerebral $A\beta$ was shown to limit cognitive loss in treated compared to control transgenic mice expressing a mutated, human, APP gene (Morgan et al, Nature 2000, 408:982–5; Janus et al, Nature 2000, 408:979–82). These results have led to clinical trials testing whether active immunization with $A\beta_{42}$ can convey therapeutic benefits to AD patients. The potential success of this strategy is thought to depend on the capacity of the immune system in AD patients to produce anti-$A\beta_{42}$.

The ability of anti-$A\beta_{42}$ antibodies to decrease the deposition of the cerebral amyloid peptides and thereby prevent or delay the development of AD-like neuropathology in mice raised, but left unanswered, the question of whether a similar mechanism could operate in AD. In particular, we considered whether AD patients might have lower levels of spontaneous serum anti-$AB_{42}$ antibodies than comparably aged normal controls. We measured serum levels of anti-$AP_{42}$ antibodies in fresh-frozen serum from 39 patients with late-onset AD (mean age=73.2±8.2) and 39 elderly adults without AD (mean age=77.7±10.8). Patients with AD were living in the community, had mild to moderate intellectual impairment, and met the NINCDS-ADRDA criteria for Probable AD. Serum from normal controls was obtained from elderly volunteers and spouses of patients who be gave informed consent to undergo neuropsychological testing and blood drawing. The serum levels of anti-$A\beta_{42}$ antibodies were measured by an ELISA using a commercially available $A\beta_{42}$ (Biosource International, Camarillo, Calif., USA). Anti-$A\beta_{42}$ antibody levels in serum from study subjects were determined in three independent assays. In each assay, the antibody level in the subject was compared to that of the same reference serum from an individual without AD. Because anti-$A\beta_{42}$ antibodies levels in serum varied 1000-fold and were not normally distributed, a statistically stringent analysis of anti-$A\beta_{42}$ antibody concentrations above or below the reference serum was carried out using the non-parametric Chi square as well as a rank order Mann-Whitney test or T-tests on log transformations of the data. Seventy-seven percent of AD patients in our sample had low levels of serum anti-$A\beta_{42}$ antibody, below that of the standard serum, a significantly smaller percentage than that found in healthy, elderly controls. The mean reciprocal titers of both anti-A$\beta$ total Ig and anti-A$\beta$ IgG were significantly lower in AD patients than elderly adults without AD as determined by T-test and Mann-Whitney test (Table 1). The difference was most significant in the case of anti-A$\beta$ IgG antibodies.

TABLE 1*

Ig and IgG anti-A$\beta_{42}$ Antibody Titer is Lower in Serum from AD Patients than Elderly Controls*
(Reciprocal Titer and 95% confidence interval)

|  | Elderly Controls (n = 39) | AD Patients (n = 39) | Statistical Test | |
|---|---|---|---|---|
|  |  |  | T Test | Mann-Whitney |
| Ig anti-A$\beta_{42}$ | 117 (70–200) | 50 (30–80) | p < 0.02 | p < 0.04 |
| IgG anti-A$\beta_{42}$ | 724 (440–1200) | 295 (180–490) | p < 0.01 | p < 0.02 |

*Coded sera were tested for anti-A$\beta_{42}$ peptide antibodies using an ELISA assay. Microtiter wells were coated with A$\beta_{42}$ washed, blocked, and incubated with 3-fold dilutions of the serum. The plates were then washed and incubated with alkaline phosphatase-conjugated goat anti-human immunoglobulin antibody. The plates were washed and incubated with enzyme substrate p-Nitrophenylphosphate. The concentration of anti-A$\beta_{42}$ peptide antibodies was the dilution of serum that gave half maximal binding and classified as being more or less than concentration of anti-A$\beta_{42}$ peptide antibodies in the reference serum.

The apolipoprotein E (ApoE)-e4 allele, a recognized risk factor for AD, was present in 51% of the patients with AD and 15% of the normal elderly in this study. The percentage of individuals with low serum anti-A$\beta_{42}$ antibody levels was greater in ApoE-e4 carriers. However, in non-ApoE-e4 carriers, a low level of serum anti-A$\beta_{42}$ IgG antibodies was significantly associated with AD (Table 2). Thus, lower serum anti-A$\beta_{42}$ antibodies is significantly associated with AD independent of ApoE genotype.

TABLE 2

IgG anti-A$\beta_{42}$ Antibody Titer is Lower in Serum from in AD Patients than in Elderly Controls not Expressing Apoprotein E4
(Reciprocal Titer and 95% confidence interval)

|  | Controls E4-Negative (n = 33) | AD E4-Negative (n = 19) | Statistic | |
|---|---|---|---|---|
|  |  |  | T Test | Mann-Whitney Test |
| Ig Anti-A$\beta_{42}$ | 112 (79–190) | 67 (34–132) | p < 0.230 | p < 0.240 |
| IgG anti-A$\beta_{42}$ | 745 (447–1251) | 297 (152–580) | p < 0.025 | p < 0.033 |

*Anti-A$\beta_{42}$ antibodies in patients and age-matched controls expressing apolipoprotein E4 gene were compared. The level of serum anti-A$\beta_{42}$ antibodies was determined and analyzed as described in the Legend to Table 1. In addition, the values above and below the median value of the total sample were counted.

The association of a low level of serum anti-A$\beta_{42}$ antibodies with AD raises the interesting possibility that AD, and conceivably other forms of dementia, may be associated with an impaired immune response to A$\beta_{42}$. Previously published results are consistent with this hypothesis (Trieb et al, Neurobiol. Aging 1996, 17:541–7). Thus, T cells from AD patients had no proliferative response or a very low proliferative response when cultured with A$\beta_{42}$. In contrast, T cells from young or old healthy individuals, cultured similarly, had a significant proliferative response. This impaired proliferative response of T cells from AD patients was not due to a generalized defect as T cells from AD patients responded as well as those from young and old individuals when cultured with the non-specific mitogen, OKT-3 antibody.

Our present data have implications for clinical trials now underway using active immunization with A$\beta_{42}$. Thus, AD patients with low serum levels of spontaneous anti-A$\beta_{42}$ antibodies may not, despite immunization with A$\beta_{42}$, develop therapeutic titers of anti-A$\beta_{42}$ antibodies. This may reflect either impaired immunity to or immune "tolerance" of A$\beta_{42}$. Impaired immunity due to decreased T helper function is suggested by the decreased proliferative response of T cells from AD patients to A$\beta_{42}$. For this reason, it may be difficult to induce an anti-A$\beta_{42}$ antibody response in AD patients. However, passive immunity, induced by the administration of human anti-A$\beta_{42}$ antibodies, especially antibodies isolated from healthy humans or healthy humans' B cells, would not depend on the recipient's immune response to A$\beta_{42}$. Thus, passive immunization could represent a viable approach to the treatment or prevention of AD in those patients who cannot generate a significant anti-A$\beta_{42}$-antibody response.

EXAMPLE 2

Evidence of Lower Anti-Amyloid Antibody Levels in Other Neurological Diseases

Forty one patients with AD had significantly (p<0.01) lower serum anti-A$\beta_{42}$ antibody levels than did 42 age-matched healthy controls or one arbitrarily selected standard (Table 3). Patients with other neurological diseases were also compared to age-matched healthy controls. Seven of eight patients with other neurological diseases had lower serum anti-A$\beta_{42}$ antibody levels than did the 21 controls in this experiment. While not statistically significant, these data indicate that significantly lower serum anti-AP$_{42}$ antibody levels in AD are specific for AD or for neurological disease.

TABLE 3

|  |  | AD | NORMAL | Other |  |
|---|---|---|---|---|---|
| 1st Set | Above MW | 2 | 10 | 0 | Cell < 5 Fisher Exact 2 tailed P value: 0.009 |
|  | Below MW | 7 | 2 | 0 |  |
| 2nd Set | Above MW | 6 | 9 | 1 | Chi Square with Yates Correction: 0.73 for Ad VS Normal Cell < 5 Fisher Exact 2 tailed P value: 0.2 for Other Vs Normal |
|  | Below MW | 17 | 12 | 7 |  |
| 3rd Set | Above MW | 2 | 4 | 0 | Cell < 5 Fisher Exact 2 tailed P value: 0.62 |
|  | Below MW | 7 | 5 | 0 |  |
| 4th Set | Above MW | 10 | 23 |  | Chi Square with Yates Correction: 0.009 |
|  | Below MW | 31 | 19 |  |  |

AD = test results for samples from Alzheimer Disease patients
Normal = test results for samples from normal patients
Other = test results from patients with other neuropathies (Parkinson's; Huntington's)
MW = arbitrary normal serum sample.

EXAMPLE 3

Reproducibility of ELISA Results

To find out the reproducibility of the ELISA essay, triplicates of sera from 3 normal subjects were coded and assayed blindly. We were able to group the 9 specimens to identify specimens coming from each of the 3 subjects. Furthermore, when the assay was performed the following day, the triplicate from the same subjects could again be identified. The rank of the subjects was identical to on day 1 and day 2 (Table 4).

| Sample | Titer | Standard-Deviation |
|--------|-------|--------------------|
| Day 1: | | |
| 43 | 0.26 | 0.03 |
| | 0.28 | |
| | 0.32 | |
| 61 | 1.06 | 0.10 |
| | 1.20 | |
| | 1.25 | |
| 1 | 11.20 | 1.59 |
| | 13.75 | |
| | 14.12 | |
| Day 2: | | |
| 43 | 0.20 | 0.17 |
| | 0.20 | |
| | 0.50 | |
| 61 | 1.20 | 0.57 |
| | 1.24 | |
| | 2.20 | |
| 1 | 16.70 | 1.31 |
| | 18.50 | |
| | 19.26 | |

These data show that the ELISA essay is highly reproducible. It is not the distribution of results on the same serum changes in repeated essay. Thus, the standard deviation in 2 out of 3 samples increased on day 2, while one sample remained approximately the same.

The present invention is not to be limited in scope by the specific escribed herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclourses of which are incorporated herein by reference in their entireties for all purposes.

What is claimed is:

1. A method for assessing risk of Alzheimer's Disease in a subject, which method comprises:
   determining the level of anti-β-amyloid-42 ($A\beta_{42}$) antibody in a biological sample selected from the group consisting of blood, serum, and plasma from a subject,
   comparing the level of anti-$A\beta_{42}$ antibody in the biological sample from the subject to a normal level determined from an average of the level of anti-$A\beta_{42}$ antibody in a biological sample from a population consisting of age-matched normal subjects who do not show any symptoms of neurodegenerative disease or disorder associated with amyloidosis, wherein a statistically simificantly lower level in the biological sample from the subject indicates the risk of Alzheimer's Disease.

2. The method according to claim 1, which comprises determining the level of anti-$A\beta_{42}$ antibody in the biological sample by immunoassay.

3. The method according to claim 2, wherein the immunoassay is an enzyme-linked immunosorbent assay.

4. The method according to claim 1, wherein the subject is from a family that has a member or members with familial Alzheimer's Disease.

5. The method according to claim 1, wherein the subject is in his or her seventh or eighth decade of life.

6. A method for assessing risk of Alzheimer's Disease in a subject, which method comprises:
   determining the level of anti-β-amyloid-42 ($A\beta_{42}$) antibody in a biological sample selected from the group consisting of blood, serum, and plasma from a subject, wherein the subject does not exhibit symptoms of cognitive dysfunction or memory dysfunction,
   comparing the level of anti-$A\beta_{42}$ antibody in the biological sample to a normal level determined from an average of the level of anti-$A\beta_{42}$ antibody in a biological sample from a population consisting of age-matched normal subjects who do not show any symptoms associated with Alzheimer's Disease, wherein a statistically significantly lower level in the biological sample from the subject indicates the risk of Alzheimer's Disease.

7. The method according to claim 6, wherein the subject is from a family that has a member or members with familial Alzheimer's Disease.

8. The method according to claim 6, wherein the subject is in his or her seventh or eighth decade of life.

* * * * *